(12) United States Patent
Sesing et al.

(10) Patent No.: US 7,897,806 B2
(45) Date of Patent: Mar. 1, 2011

(54) METHOD FOR PRODUCING POLYISOCYANATES

(75) Inventors: Martin Sesing, Waldsee (DE); Thorsten Rohde, Mannheim (DE); Eckhard Stroefer, Mannheim (DE); Jochem Henkelmann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 971 days.

(21) Appl. No.: 11/718,518

(22) PCT Filed: Oct. 27, 2005

(86) PCT No.: PCT/EP2005/011490
§ 371 (c)(1),
(2), (4) Date: May 3, 2007

(87) PCT Pub. No.: WO2006/048171
PCT Pub. Date: May 11, 2006

(65) Prior Publication Data
US 2009/0112017 A1    Apr. 30, 2009

(30) Foreign Application Priority Data
Nov. 3, 2004   (DE) .......................... 10 2004 053 662

(51) Int. Cl.
*C07C 263/10* (2006.01)
*C07C 265/12* (2006.01)
*C07C 265/14* (2006.01)

(52) U.S. Cl. ....................................................... 560/347

(58) Field of Classification Search .................. None
See application file for complete search history.

(56) References Cited

U.S. PATENT DOCUMENTS

| 2004/0024244 A1 | 2/2004 | Walsdorff et al. |
| 2004/0073035 A1 | 4/2004 | Maase et al. |
| 2004/0133058 A1 | 7/2004 | Arlt et al. |

FOREIGN PATENT DOCUMENTS

| DE | 1 192 641 | 10/1963 |
| DE | 100 27 779 | 12/2001 |
| DE | 102 02 838 | 8/2003 |
| WO | 01 91898 | 12/2001 |
| WO | 02 02217 | 1/2002 |
| WO | 02 074718 | 9/2002 |

OTHER PUBLICATIONS

Earle et al. Organic Letters, 2004, 6(5), 707-710.*
Schauerte, K. et al.,"Handbuch, Kunststoff 7 (Polyurethane), 3$^{rd}$ new Ed.," Carl-HANSER-Verlag, Munchen-Wien, pp. 76-88, 1993.
Wasserscheid, P., et al., "Ionische Flussigkeiten -neue"Losungen" fur die Ubergangsmetallkatalyse", Angewandte Chemie, vol. 112, pp. 3926-3945, 2000.
Wu, B. et al., "Novel Ionic Liquid Thermal Storage for solar Thermal Electric Power System", Proceeding of solar Forum, 2001.
U.S. Appl. No. 12/446,460, filed Apr. 21, 2009, Boehling, et al.

* cited by examiner

*Primary Examiner* — Daniel M Sullivan
*Assistant Examiner* — Yevegeny Valenrod
(74) *Attorney, Agent, or Firm* — Oblon, Spivak, McClelland, Maier & Neustadt, L.L.P.

(57) ABSTRACT

The invention relates to a process for preparing polyisocyanates by reacting primary amines with phosgene in the presence of a solvent, wherein ionic liquids are used as solvents.

6 Claims, No Drawings

METHOD FOR PRODUCING POLYISOCYANATES

The invention relates to a process for preparing polyisocyanates by reacting the corresponding amines with phosgene.

Polyisocyanates are prepared in large quantities and serve mainly as starting materials for producing polyurethanes. They are usually prepared by reacting the corresponding amines with phosgene.

The continuous preparation of organic polyisocyanates by reaction of primary organic amines with phosgene has been described many times and is carried out on a large industrial scale (cf., for example, Ullmanns Enzyklopädie der Technischen Chemie, and 7 (Polyurethane), 3rd Revised Edition, Carl Hanser Verlag, Munich-Vienna, p. 76ff (1993)). The aromatic isocyanates TDI (tolylene diisocyanate) and MDI (methylenedi(phenyl isocyanate) or PMDI (polymethylenepolyphenylene polyisocyanate) in particular and also the aliphatic isocyanates HDI (hexamethylenedi(phenyl isocyanate) and isophorone diisocyanate (IPDI) are produced industrially.

The continuous embodiment of this process is generally carried out in two stages. In the first stage of the phosgenation, the amine is reacted with phosgene to form carbamoyl chloride and hydrogen chloride and, in a parallel reaction, amine hydrochloride. The reaction between amine and phosgene is very fast, strongly exothermic and proceeds even at very low temperatures. To minimize formation of by-products and solids, amine and phosgene therefore have to be mixed very quickly, if appropriate in admixture with an organic solvent. The first phosgenation stage is therefore generally carried out in a mixing device, preferably a nozzle. The second stage of the phosgenation comprises both the decomposition of the carbamoyl chloride, which is usually present as a solid, to form the desired isocyanate and hydrogen chloride and also the phosgenation of the amine hydrochloride to form the carbamoyl chloride. The temperature in the second phosgenation stage is generally higher than that in the first. Many reactors have been developed for the second stage.

The hydrogen chloride formed in the reaction is usually removed very quickly from the reaction mixture in order to reduce the pressure in the reaction system and to shift the equilibrium of the reaction in the direction of the isocyanates.

The rate of the reaction of phosgene with amine or of hydrogen chloride with amine depends predominantly on the type of isocyanate to be prepared and on the reaction temperature chosen.

In the cold-hot phosgenation, amine hydrochlorides are formed as intermediates and react further in a slow solid/liquid reaction. Modern nozzle methods, for example as described in WO 02/02217 and WO 01/91898, operate exclusively according to the principle of hot phosgenation in which amine hydrochloride nanoparticles having a large surface area are formed as intermediates. These particles react with phosgene in a subsequent reaction to form the desired product. The reaction of the solids with the phosgene proceeds very slowly. In addition, there is a risk of the solids leading to blockages in the plant.

The preparation of the isocyanates is usually carried out in solution. Here, the starting materials are dissolved in the solvents which are inert toward the starting materials and end products, the solutions are reacted with one another and the solvent is subsequently separated off.

As solvents, preference is given to using chlorinated aromatic hydrocarbons such as dichlorobenzene, chlorobenzene, trichlorobenzene or aromatic or aliphatic hydrocarbons such as toluene, xylene, benzene, pentane, hexane, heptane, octane, cyclohexane, biphenyl, ketones such as 2-butanone, methyl isobutyl ketone, esters such as diethyl isophthalate, ethyl acetate, butyl acetate, nitriles such as acetonitrile, or sulfolane, etc. However, the solubility of the amine hydrochlorides and carbamoyl chlorides formed as intermediates is frequently unsatisfactory.

The use of the isocyanates themselves as solvents is known from DE 11 92 641 and DE 100 27 779. Isocyanate as solvent has the advantage of a higher polarity than the inert solvents customarily used. Salt-like solids formed as intermediates are therefore dissolved better. However, a disadvantage is the formation of ureas by reaction of the isocyanates used as solvent with the amines.

A possible way of improving the solubility of the solids would be the use of strongly polar solvents such as alcohols. However, this would lead to such a high level of secondary reactions that it is ruled out from an industrial point of view.

A continual demand in the preparation of isocyanates by reacting the corresponding amines with phosgene is to reduce the amount of phosgene present in the reaction system, also known was phosgene holdup. A further continual demand in the preparation of polyisocyanates is to reduce secondary reactions and thus to obtain a higher yield and products having improved quality.

It was an object of the invention to develop a process for preparing polyisocyanates by reacting amines with phosgene, in which the formation of solids is minimized without secondary reactions occurring. Furthermore, the reaction should be possible at low pressures and/or temperatures. This would result in a lower phosgene holdup, higher space-time yields and better selectivities.

This object has surprisingly been able to be achieved by using ionic liquids as solvents.

The invention accordingly provides a process for preparing polyisocyanates by reacting primary amines with phosgene in the presence of a solvent, wherein ionic liquids are used as solvents.

For the purposes of the present invention, ionic liquids are compounds which have at least one cationic center and at least one anionic center, in particular at least one cation and at least one anion, with one of the ions, in particular the cation, being organic.

According to the definition of Wasserscheid and Keim in: Angewandte Chemie 2000, 112, 3926-3945, ionic liquids are salts which melt at relatively low temperatures and have a nonmolecular, ionic character. They are liquid at relatively low temperatures and here have a relatively low viscosity. They possess very good solvent capabilities for a large number of organic, inorganic and polymeric substances. Furthermore, they are generally noncombustible, noncorrosive and have no measurable vapor pressure.

Ionic liquids are compounds which are made up of positive and negative ions but have no overall charge. Both the positive ions and the negative ions are predominantly monovalent, but multivalent anions and/or cations, for example ions having from one to five, preferably from one to four, more preferably from one to three and very particularly preferably one or two, electric charges per ion, are also possible. The charges can be located on various localized or delocalized regions within a molecule, i.e. in a betaine-like fashion, or can be present as separate anions and cations. Preference is given to ionic liquids which are made up of at least one cation and at least one anion.

Known fields of use for ionic liquids are, in particular, as solvents for chemical reactions, as auxiliaries for separating acids from chemical reaction mixtures as described in DE 10202838, as auxiliaries for extractive rectification for the separation of close-boiling or azeotropic mixtures as described in WO 02/074718 or as heat transfer media in solar units, corresponding to the description in Proceedings of Solar Forum, 2001, Apr. 21 to 25, Washington, D.C.

The invention is not restricted to specific ionic liquids; it is possible to use all suitable ionic liquids, including mixtures of various ionic liquids.

Preference is given to ionic liquids having a very low melting point, in particular below 150° C., more preferably below 100° C., particularly preferably below 80° C.

The ionic liquid which functions as reaction medium is preferably selected so that it is largely inert toward the substances participating in the reaction, is present as a liquid under the reaction conditions, has a solvent capability for the products and intermediates formed in the reaction which is sufficient for the reaction, in particular a good solvent capability for the amine hydrochloride and carbamoyl chloride formed as intermediates, has an anion whose corresponding acid is less volatile than the hydrogen chloride formed in the reaction and preferably allows the product to be separated off by formation of a second phase with the reaction product or by extraction with a further solvent in which the ionic liquid is largely insoluble.

Preference is given to ionic liquids of the general formula $$[A]_n^+[Y]^{n-}$$

where n=1, 2, 3 or 4 and
the cation [A] is selected from among
    quaternary ammonium cations of the general formula,

phosphonium cations of the general formula,

imidazolium cations of the general formula,

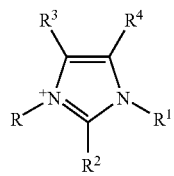

and also all isomeric imidazolinium cations and imidazolidinium cations which are analogous to the above formula,
H-pyrazolium cations of the general formula,

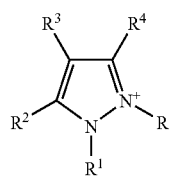

and also 3H-pyrazolium cations, 4H-pyrazolium cations, 1-pyrazolinium cations, 2-pyrazolinium cations and 3-pyrazolinium cations,
    pyridinium cations of the general formula,

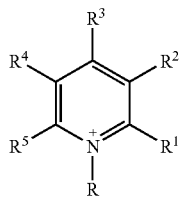

and also pyridazinium, pyrimidinium and pyrazinium ions, pyrrolidinium cations of the general formula,

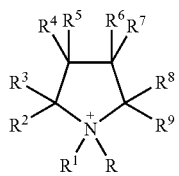

guanidinium cations of the general formula,

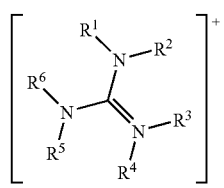

five- to at least six-membered heterocyclic cations which have at least one phosphorus or nitrogen atom and optionally an oxygen or sulfur atom, for example thiazolium, oxazolium, 1,2,4-triazolium or 1,2,3-triazolium, particularly preferably compounds containing at least one five- or six-membered heterocycle which has one, two or three nitrogen atoms and a sulfur atom or an oxygen atom, very particularly preferably compounds of this type having one or two nitrogen atoms,
the 1,8-diazabicyclo[5.4.0]undec-7-enium cation and the 1,8-diazabicyclo-[4.3.0]non-5-enium cation:

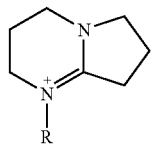

and oligomers and polymers in which these cations are present, where the radicals R, $R^1$, $R^2$, $R^3$, $R^4$, $R^5$, $R^6$, $R^7$, $R^8$ and $R^9$ are each, independently of one another, hydrogen, C1-C18-alkyl, C2-C18-alkyl which may be interrupted by one or more oxygen and/or sulfur atoms and/or one or more substituted or unsubstituted imino groups, C6-C12-aryl, C5-C12-cycloalkyl or a five- to six-membered, oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles.

Here, $C_1$-$C_{18}$-alkyl which may be substituted by functional groups, aryl, alkyl, aryloxy, alkyloxy, halogen, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzohydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and $C_2$-$C_{18}$-alkyl which may be interrupted by one or more oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, these radicals can together be 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups is not subject to any restrictions. In general, it is not more than 5 in the radical, preferably not more than 4 and very particularly preferably not more than 3.

Furthermore, at least one carbon atom, preferably at least two carbon atoms, is/are generally present between any two heteroatoms.

Substituted and unsubstituted imino groups can be, for example, imino, methylimino, isopropylimino, n-butylimino or tert-butylimino.

Furthermore, functional groups are carboxy, carboxamide, hydroxy, di($C_1$-$C_4$-alkyl)amino, $C_1$-$C_4$-alkyloxycarbonyl, cyano or $C_1$-$C_4$-alkyloxy, $C_6$-$C_{12}$-aryl which may be substituted by functional groups, aryl, alkyl, aryloxy, alkyloxy, halogen, heteroatoms and/or heterocycles is, for example, phenyl, tolyl, xylyl, α-naphthyl, α-naphthyl, 4-diphenylyl, chlorophenyl, dichlorophenyl, trichlorophenyl, difluorophenyl methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl which may be substituted by functional groups, aryl, alkyl, aryloxy, alkyloxy, halogen, heteroatoms and/or heterocycles is, for example, cyclopentyl, cyclohexyl, cyclooctyl, cyclododecyl, methyl cyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl, a five- or six-membered, oxygen-, nitrogen- and/or sulfur-containing heterocycle is, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tertbutylthiophenyl and $C_1$-$C_4$-alkyl is, for example, methyl, ethyl, propyl, isopropyl, n-butyl, sec-butyl or tert-butyl.

Preference is given to R, $R^1$, $R^2$, $R^3$, $R^4$, $R^5$, $R^6$, $R^7$, $R^8$ and $R^9$ each being, independently of one another, hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, benzyl, acetyl, dimethylamino, diethylamino and chlorine.

It is also possible to use mixed species such as

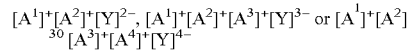

where $A^1$, $A^2$, $A^3$ and $A^4$ are selected independently from among the groups mentioned for [A].

In addition, it is possible to use mixed species having metal cations

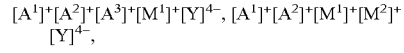

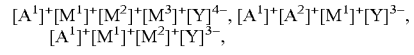

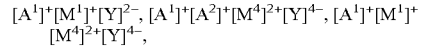

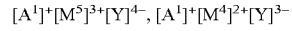

where $M^1$, $M^2$, $M^3$ are monovalent metal cations, $M^4$ is a divalent metal cation and $M^5$ is a trivalent metal cation.

As anions, it is in principle possible to use all anions.

The anion [Y] is preferably selected from the group consisting of halides and halogen-containing compounds of the formulae:

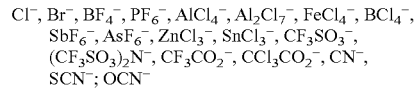

the group consisting of sulfates, sulfites and sulfonates of the general formulae:

$$SO_4^{2-}, HSO_4^-, SO_3^{2-}, HSO_3^-, R^aOSO_3^-, R^aSO_3^-$$

the group consisting of phosphates of the general formulae:

$$PO_4^{3-}, HPO_4^{2-}, H_2PO_4^-, R^aPO_4^{2-}, HR^aPO_4^-, R^aR^bPO_4^-$$

the group consisting of phosphonates and phosphinates of the general formulae:

$$R^aHPO_3^-, R^aR^bPO_2^-, R^aR^bPO_3^-$$

the group consisting of phosphites of the general formulae:

$$PO_3^{3-}, HPO_3^{2-}, H_2PO_3^-, R^aPO_3^{2-}, R^aHPO_3^-, R^aR^bPO_3$$

the group consisting of phosphonites and phosphinites of the general formulae:

$$R^aR^bPO_2^-, R^aHPO_2^-, R^aR^bPO^-, R^aHPO^-$$

the group consisting of carboxylic acids of the general formula:

$$R^aCOO^-$$

the group consisting of borates of the general formulae:

$$BO_3^{3-}, HBO_3^{2-}, H_2BO_3^-, R^aR^bBO_3^-, R^aHBO_3^-, R^aBO_3^{2-}$$

the group consisting of boronates of the general formulae:

$$R^aBO_2^{2-}, R^aR^bBO^-$$

the group consisting of carbonates and carbonic esters of the general formulae:

$$HCO_3^-, CO_3^{2-}, R^aCO_3^-$$

the group consisting of silicates and silicic esters of the general formulae:

$$SiO_4^{4-}, HSiO_4^{3-}, H_2SiO_4^{2-}, H_3SiO_4^-, R^aSiO_4^{3-},$$
$$R^aR^bSiO_4^{2-}, R^aR^bR^cSiO_4^-, HR^aSiO_4^{2-},$$
$$H_2R^aSiO_4^-, HR^aR^bSiO_4^-$$

the group consisting of alkylsilane and arylsilane salts of the general formulae:

$$R^aSiO_3^{3-}, R^aR^bSiO_2^{2-}, R^aR^bR^cSiO^-, R^aR^bR^cSiO_3^-,$$
$$R^aR^bR^cSiO_2^-, R^aR^bSiO_3^{2-}$$

the group consisting of carboximides, bis(sulfonyl)imides and sulfonylimides of the general formulae:

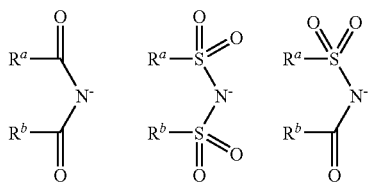

the group consisting of alkoxides and aryloxides of the general formula:

$$R^aO^-$$

the group consisting of complex metal ions such as $Fe(CN)_6^{3-}$, $Fe(CN)_6^{4-}$, $MnO_4^-$, $Fe(CO)_4$ and the radicals $R^a$, $R^b$, $R^c$ are each, independently of one another, C1-C18-alkyl, C2-C18-alkyl which may be interrupted by one or more oxygen and/or sulfur atoms and/or one or more substituted or unsubstituted imino groups, C6-C12-aryl, C5-C12-cycloalkyl or a five- or six-membered, oxygen-, nitrogen- and/or sulfur-containing heterocycle or two of them together form an unsaturated, saturated or aromatic ring which may be interrupted by one or more oxygen and/or sulfur atoms and/or one or more substituted or unsubstituted imino groups, where the radicals mentioned may each be substituted by functional groups, aryl, alkyl, aryloxy, alkyloxy, halogen, heteroatoms and/or heterocycles.

Here, $C_1$-$C_{18}$-alkyl which may be substituted by functional groups, aryl, alkyl, aryloxy, alkyloxy, halogen, heteroatoms and/or heterocycles is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, hexadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzohydryl, p-tolylmethyl, 1-(p-butylphenyl)ethyl, chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, and $C_2$-$C_{18}$-alkyl which may be interrupted by one or more oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

If two radicals form a ring, these radicals can together be 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulfur atoms and/or imino groups is not subject to any restrictions. In general, it is not more than 5 in the radical, preferably not more than 4 and very particularly preferably not more than 3.

Furthermore, at least one carbon atom, preferably at least two carbon atoms, is/are generally present between any two heteroatoms.

Substituted and unsubstituted imino groups can be, for example, imino, methylimino, isopropylimino, n-butylimino or tert-butylimino.

Furthermore, functional groups are carboxy, carboxamide, hydroxy, di($C_1$-$C_4$-alkyl)amino, $C_1$-$C_4$-alkyloxycarbonyl, cyano or $C_1$-$C_4$-alkyloxy, $C_6$-$C_{12}$-aryl which may be substituted by functional groups, aryl, alkyl, aryloxy, alkyloxy, halogen, heteroatoms and/or heterocycles is, for example, phenyl, tolyl, xylyl, α-naphthyl, α-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, isopropylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl which may be substituted by functional groups, aryl, alkyl, aryloxy, alkyloxy, halogen, heteroatoms and/or heterocycles is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl or a saturated or unsaturated bicyclic system such as norbornyl or norbornenyl, a five- or six-membered, oxygen-, nitrogen- and/or sulfur-containing heterocycle is, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tertbutylthiophenyl and $C_1$-$C_4$-alkyl is, for example, methyl, ethyl, propyl, isopropyl, n-butyl, sec-butyl or tert-butyl.

Preference is given to $R^1$, $R^2$, $R^3$, $R^4$ and $R^5$, each being, independently of one another, hydrogen, methyl, ethyl, n-butyl, 2-hydroxyethyl, 2-cyanoethyl, 2-(methoxycarbonyl)ethyl, 2-(ethoxycarbonyl)ethyl, 2-(n-butoxycarbonyl)ethyl, dimethylamino, diethylamino and chlorine.

In the process of the invention, the cations are preferably selected from the group consisting of 1,2,3-trimethylimidazolium, 1,3,4,5-tetramethylimidazolium, 1,3,4-dimethylimidazolium, 1,3,4-trimethylimidazolium, 1,3-dibutyl-2-methylimidazolium, 1,3-dbutylimidazolium, 1,2-dimethylimidazolium, 1,3-dimethylimidazolium, 1-benzyl-3-methylimidazolium, 1-butyl-2,3-dimethylimidazolium, 1-butyl-2-ethyl-5-methylimidazolium, 1-butyl-2-ethylimidazolium, 1-butyl-2-methylimidazolium, 1-butyl-3,4,5-trimethylimidazolium, 1-butyl-3,4-dimethylimidazolium, 1-butyl-3-ethylimidazolium, 1-butyl-3-methylimidazolium, 1-butyl-4-methylimidazolium, 1-butylimidazolium, 1-decyl-3-methylimidazolium, 1-dodecyl-3-methylimidazolium, 1-ethyl-2,3-dimethylimidazolium, 1-ethyl-3-methylimidazolium 1-hexadecyl-2,3-dimethylimidazolium, 1-hexadecyl-3-methylimidazolium, 1-hexyl-2,3-dimethylimidazolium, 1-hexyl-3-methylimidazolium, 1-methyl-2-ethylimidazolium, 1-methyl-3-octylimidazolium, 1-methylimidazolium, 1-pentyl-3-methylimidazolium, 1-phenylpropyl-3-methylimidazolium, 1-propyl-2,3-dimethylimidazolium, 1-tetradecyl-3-methylimidazolium, 2,3-dimethylimidazolium, 2-ethyl-3,4-dimethylimidazolium, 3,4-dimethylimidazolium, 1,2-dimethylpyridinium, 1-butyl-2-ethyl-6-methylpyridinium, 1-butyl-2-ethylpyridinium, 1-butyl-2-methylpyridinium, 1-butyl-3,4-dimethylpyridinium, 1-butyl-3,5-dimethylpyridinium, 1-butyl-3-ethylpyridinium, 1-butyl-3-methylpyridinium, 1-butyl-4-methylpyridinium, 1-butylpyridinium, 1-ethylpyridinium, 1-hexyl-3-methylpyridinium, 1-hexyl-4-methylpyridinium, 1-hexylpyridinium, 1-methylpyridinium, 1-octylpyridinium, 2-ethyl-1,6-dimethylpyridinium, 2-ethyl-1-methylpyridinium, 4-methyl-1-octylpyridinium, 1,1-dimethylpyrrolidinium, 1-butyl-1-ethylpyrrolidinium, 1-butyl-1-methylpyrrolidinium, 1-ethyl-1-methylpyrrolidinium, 1-ethyl-3-methylpyrrolidinium, 1-hexyl-1-methylpyrrolidinium, 1-octyl-1-methylpyrrolidinium, guanidinium, hexamethylguanidinium, N,N,N',N'-tetramethyl-N''-ethylguanidinium, N-pentamethyl-N-isopropylguanidinium, N-pentamethyl-N-propylguanidinium, benzyltriphenylphosphonium, tetrabutylphosphonium, trihexyl(tetradecyl)phosphonium, triisobutyl(methyl)phosphonium, butyltrimethylammonium, methyltrioctylammonium, octyltrimethylammonium, tetrabutylammonium, tetraethylammonium, tetramethylammonium, tributylmethylammonium.

Particularly preferred cations are selected from the group consisting of 1,2,3-trimethylimidazolium, 1,2-dimethylimidazolium, 1-butyl-2-methylimidazolium, 1-butyl-4-methylimidazolium, 1,3-diethylimidazolium, 1-benzyl-3-methylimidazolium, 1-butyl-2,3-dimethylimidazolium, 1-butyl-2-methylimidazolium, 1-butyl-3-ethylimidazolium, 1-butyl-3-methylimidazolium, 1-butylimidazolium, 1-ethyl-2,3-dimethylimidazolium, 1-ethyl-3-methylimidazolium, 1-hexyl-3-methylimidazolium, 1-methyl-2-ethylimidazolium, 1-methyl-3-octylimidazolium, 1-methylimidazolium, 1-decyl-3-methylimidazolium, 1-dodecyl-3-methylimidazolium, 1-butyl-4-methylpyridinium, 1-butylpyridinium, 1-ethylpyridinium, 1-hexylpyridinium, 1-butyl-1-ethylpyrrolidinium, 1-butyl-1-methylpyrrolidinium, 1-ethyl-1-methylpyrrolidinium, 1-hexyl-1-methylpyrrolidinium, guanidinium, N,N,N',N'-tetramethyl-N''-ethylguanidinium, benzyltriphenylphosphonium, tetrabutylphosphonium, butyltrimethylammonium, methyltrioctylammonium, tetrabutylammonium, tributylmethylammonium.

In particular, the cations are selected from the group consisting of 1,2,3-trimethylimidazolium, 1,2-dimethylimidazolium, 1-butyl-2,3-dimethylimidazolium, 1-butyl-3-methylimidazolium, 1-ethyl-2,3-dimethylimidazolium, 1-ethyl-3-methylimidazolium, 1-butylimidazolium, 1-methylimidazolium, 1-butyl-4-methylpyridinium, 1-butylpyridinium, methyltrioctylammonium, octyltrimethylammonium.

In the process of the invention, the anions are preferably selected from the group consisting of acetate, bis(2,4,4-trimethylpentyl)phosphinate, bis(malonato)borate, bis(oxalato)borate, bis(pentafluoroethyl)phosphinate, bis(phthalato)borate, bis(salicylato)borate, bis(trifluoromethanesulfonyl)imidate, bis(trifluoromethanesulfonyl)methane, bis(trifluoromethyl)imidate, borate, bromide, bromoaluminates, carbonate, chloride, chloroaluminates, decylbenzenesulfonate, dichlorocuprate, dicyanamide, didecylbenzenesulfonate, didodecylbenzenesulfonate, diethylphosphate, dihydrogenphosphate, dodecylbenzenesulfonate, ethylsulfate, ethylsulfonate, fluoride, hexafluorophosphate, hydrogencarbonate, hydrogenphosphate, hydrogensulfate, hydrogensulfite, iodide, methylsulfate, methylsulfonate, nitrate, nitrite, phosphate, sulfate, sulfite, tetracyanoborate, tetrafluoroborate, tetrakis(hydrogensulfato)borate, tetrakis(methylsulfonato)borate, thiocyanate, tosylate, trichlorozincate, trifluoroacetate, trifluoromethylsulfonate, tris(heptafluoropropyl)trifluorophosphate, tris(nonafluorobutyl)

trifluorophosphate, tris(pentafluoroethyl)trifluorophosphate, tris(pentafluoroethylsulfonyl)trifluorophosphate.

The anions are particularly preferably selected from the group consisting of bis(2,4,4-trimethylpentyl)phosphinate, bis(malonato)borate, bis(oxalato)borate, bis(phthalato)borate, bis(trifluoromethanesulfonyl)imidate, borate, chloride, chloroaluinmates, decylbenzenesulfonate, didecylbenzenesulfonate, didodecylbenzenesulfonate, dihydrogenphosphate, dodecylbenzenesulfonate, ethylsulfate, ethylsulfonate, hydrogensulfate, methylsulfate, methylsulfonate, phosphate, sulfate, tetrakis(methylsulfonato)borate, tosylate, trichlorozincate.

In particular, the anions are selected from the group consisting of chloride, chloroalumites, ethylsulfate, methylsulfate, methylsulfonate, sulfate, tosylate.

Preferred ionic liquids for the process of the invention are selected from the group consisting of
1,2,3-trimethylimidazolium chloride, 1,2-dimethylimidazolium chloride, 1-butyl-2,3-dimethylimidazolium chloride, 1-butyl-3-methylimidazolium chloride, 1-butylimidazolium chloride, 1-methylimidazolium chloride, 1-ethyl-2,3-dimethylimidazolium chloride, 1-ethyl-3-methylimidazolium chloride, 1-butyl-4-methylpyridinium chloride, 1-butylpyridiniumchloride, methyltrioctylammonium chloride, octyltrimethylammonium chloride, 1,2,3-trimethylimidazolium tetrachloroaluminate, 1,2-dimethylimidazolium tetrachloroaluminate, 1-butyl-2,3-dimethylimidazolium tetrachloroaluminate, 1-butyl-3-methylimidazolium tetrachloroaluminate, 1-ethyl-2,3-dimethylimidazolium tetrachloroaluminate, 1-ethyl-3-methylimidazolium tetrachloroaluminate, 1-butyl-4-methylpyridinium tetrachloroaluminate, 1-butylpyridinium tetrachloroaluminate, methyltrioctylammonium tetrachloroaluminate, octyltrimethylammonium tetrachloroaluminate, 1,2,3-trimethylimidazolium ethylsulfate, 1,2-dimethylimidazolium ethylsulfate, 1-butyl-2,3-dimethylimidazolium ethylsulfate, 1-butyl-3-methylimidazolium ethylsulfate, 1-ethyl-2,3-dimethylimidazolium ethylsulfate, 1-ethyl-3-methylimidazolium ethylsulfate, 1-butyl-4-methylpyridinium ethylsulfate, 1-butylpyridinium ethylsulfate, methyltrioctylammonium ethylsulfate, octyltrimethylammonium ethylsulfate, 1,2,3-trimethylimidazolium methylsulfate, 1,2-dimethylimidazolium methylsulfate, 1-butyl-2,3-dimethylimidazolium methylsulfate, 1-butyl-3-methylimidazolium methylsulfate, 1-ethyl-2,3-dimethylimidazolium methylsulfate, 1-ethyl-3-methylimidazolium methylsulfate, 1-butyl-4-methylpyridinium methylsulfate, 1-butylpyridinium methylsulfate, methyltrioctylammonium methylsulfate, octyltrimethylammonium methylsulfate, 1,2,3-trimethylimidazolium methylsulfonate, 1,2-dimethylimidazolium methylsulfonate, 1-butyl-2,3-dimethylimidazolium methylsulfonate, 1-butyl-3-methylimidazolium methylsulfonate, 1-ethyl-2,3-dimethylimidazolium methylsulfonate, 1-ethyl-3-methylimidazolium methylsulfonate, 1-butyl-4-methylpyridinium methylsulfonate, 1-butylpyridinium methylsulfonate, methyltrioctylammonium methylsulfonate, octyltrimethylammonium methylsulfonate, 1,2,3-trimethylimidazolium sulfate, 1,2-dimethylimidazolium sulfate, 1-butyl-2,3-dimethylimidazolium sulfate, 1-butyl-3-methylimidazolium sulfate, 1-ethyl-2,3-dimethylimidazolium sulfate, 1-ethyl-3-methylimidazolium sulfate, 1-butyl-4-methylpyridinium sulfate, 1-butylpyridinium sulfate, methyltrioctylammonium sulfate, octyltrimethylammonium sulfate, 1,2,3-trimethylimidazolium tosylate, 1,2-dimethylimidazolium tosylate, 1-butyl-2,3-dimethylimidazolium tosylate, 1-butyl-3-methylimidazolium tosylate, 1-ethyl-2,3-dimethylimidazolium tosylate, 1-ethyl-3-methylimidazolium tosylate, 1-butyl-4-methylpyridinium tosylate, 1-butylpyridinium tosylate, methyltrioctylammonium tosylate, octyltrimethylammonium tosylate.

Particularly preferred ionic liquids are selected from the group consisting of 1-butyl-2,3-dimethylimidazolium chloride, 1-butyl-3-methylimidazolium chloride, 1-butylimidazolium chloride, 1-methylimidazolium chloride, 1-ethyl-2,3-dimethylimidazolium chloride, 1-ethyl-3-methylimidazolium chloride, 1-butyl-4-methylpyridinium chloride, 1-methylpyridinium chloride, methyltrioctylammonium chloride, 1-butyl-2,3-dimethylimidazolium tetrachloroaluminate, 1-butyl-3-methylimidazolium tetrachloroaluminate, 1-ethyl-2,3-dimethylimidazolium tetrachloroaluminate, 1-ethyl-3-methylimidazolium tetrachloroaluminate, 1-butyl-4-methylpyridinium tetrachloroaluminate, 1-methylpyridinium tetrachloroaluminate, methyltrioctylammonium tetrachloroaluminate, 1-butyl-2,3-dimethylimidazolium ethylsulfate, 1-butyl-3-methylimidazolium ethylsulfate, 1-ethyl-2,3-dimethylimidazolium ethylsulfate, 1-ethyl-3-methylimidazolium ethylsulfate, 1-butyl-4-methylpyridinium ethylsulfate, 1-methylpyridinium ethylsulfate, methyltrioctylammonium ethylsulfate, 1-butyl-2,3-dimethylimidazolium methylsulfate, 1-butyl-3-methylimidazolium methylsulfate, 1-ethyl-2,3-dimethylimidazolium methylsulfate, 1-ethyl-3-methylimidazolium methylsulfate, 1-butyl-4-methylpyridinium methylsulfate, 1-methylpyridinium methylsulfate, methyltrioctylammonium methylsulfate, 1-butyl-2,3-dimethylimidazolium methylsulfonate, 1-butyl-3-methylimidazolium methylsulfonate, 1-ethyl-2,3-dimethylimidazolium methylsulfonate, 1-ethyl-3-methylimidazolium methylsulfonate, 1-butyl-4-methylpyridinium methylsulfonate, 1-methylpyridinium methylsulfonate, methyltrioctylammonium methylsulfonate.

In particular, the ionic liquids are selected from the group consisting of 1-butyl-2,3-dimethylimidazolium chloride, 1-butyl-3-methylimidazolium chloride, 1-butylimidazolium chloride, 1-methylimidazolium chloride, 1-ethyl-3-methylimidazolium chloride, 1-butyl-4-methylpyridinium chloride, methyltrioctylammonium chloride, 1-butyl-2,3-dimethylimidazolium tetrachloroaluminate, 1-butyl-3-methylimidazolium tetrachloroaluminate, 1-ethyl-3-methylimidazolium tetrachloroaluminate, 1-butyl-4-methylpyridinium tetrachloroaluminate, methyltrioctylammonium tetrachloroaluminate, 1-butyl-2,3-dimethylimidazolium methylsulfate, 1-butyl-3-methylimidazolium methylsulfate, 1-ethyl-3-methylimidazolium methylsulfate, 1-butyl-4-methylpyridinium methylsulfate, methyltrioctylammonium methylsulfate, 1-butyl-2,3-dimethylimidazolium methylsulfonate, 1-butyl-3-methylimidazolium methylsulfonate, 1-ethyl-3-methylimidazolium methylsulfonate, 1-butyl-4-methylpyridinium methylsulfonate, methyltrioctylammonium methylsulfonate.

In a particular embodiment of the invention, an anionic liquid in admixture with hydrogen chloride is used as solvent. The ratio of hydrogen chloride to ionic liquid in this embodiment is from >0 to 400 mol %, preferably from 5 to 300 mol %, very particularly preferably from 10 to 150 mol %, based on the ionic liquid.

It has surprisingly been found that the ionic liquids used according to the invention as solvents have a high solvent capability, in particular for the amine hydrochlorides and carbamoyl chlorides, that they induce an acceleration of the reaction, in particular the phosgenation of amine hydrochlorides, and that they can be separated from the end products by simple distillation or extraction.

The customary polyisocyanates prepared on a large industrial scale can be prepared by the process of the invention. These are, for example, the aromatic isocyanates TDI (tolylene diisocyanate) and MDI (methylenedi(phenyl isocyanate)), PMDI (polymethylenepolyphenylene polyisocyanate) and mixtures of MDI and PMDI (crude MDI) and also the aliphatic isocyanates HDI (hexamethylenedi(phenyl isocyanate)) and isophorone diisocyanate (IPDI).

The temperature range which is advantageous for the process of the invention depends, inter alia, on the type and amount of solvent and on the isocyanate to be prepared. In general, the temperature in the mixing unit is from −20° C. to 300° C., preferably from 10° C. to 200° C. and particularly preferably from 80° C. to 150° C. The temperature in the reactor is generally from 10° C. to 360° C. and preferably from 40° C. to 210° C. and particularly preferably from 80° C. to 150° C. In addition, the absolute pressure is generally in the range from 0.2 bar to 50 bar, preferably from 0.8 bar to 25 bar, particularly preferably from 1 to 17 bar.

The total residence time of the liquid in the mixing device and in the reactor is from 12 s to 20 mm, preferably in the range from 36 s to 16 mm, and particularly preferably from 60 s to 12 mm.

The molar ratio of phosgene used to amino groups is from 1:1 to 12:1, preferably from 1.1:1 to 6:1.

To carry out the process of the invention, the starting materials amine or amine hydrochloride and phosgene are dissolved in the ionic liquid used as solvent. As an alternative to this, it is also possible for only the amine or the amine hydrochloride to be dissolved in the ionic liquid. The stream comprising amine or amine hydrochloride dissolved in the ionic liquid is combined with the phosgene which can either be dissolved in the ionic liquid or be in pure form, preferably in a mixing nozzle. In a preferred embodiment, an axially symmetric mixing tube apparatus into which amine is introduced axially and phosgene is introduced via two nonaxial annular gaps is used as mixing nozzle.

In a further embodiment of the invention, the amine can also be dissolved as amine hydrochloride in the ionic liquid and mixed with the phosgene (pure or in solution). In contrast to the classical processes, it is not absolutely necessary for mixing to be carried out very quickly, since the further reaction of the isocyanate with the amine to form urea proceeds very much more slowly via the intermediate stage of the hydrochloride.

The reaction can in this case advantageously be carried out at a low pressure. As reactors, it is possible to use, for example, sparged stirred vessels or bubble column reactors. The hydrogen chloride formed in the reaction can be discharged continuously from the process.

In a further embodiment of the process of the invention, phosgene which is recirculated from the reaction and still contains hydrogen chloride is used for preparing the phosgene-containing solution. In this embodiment, the process step corresponding to the prior art for separating phosgene and hydrogen chloride after the preparation of the isocyanates can be omitted.

The amount of ionic liquid used as solvent in the process of the invention is generally from 10 to 1000% by weight, preferably from 50 to 500% by weight, more preferably from 100 to 400% by weight, based on the amount of amine used.

After the reaction, the reaction mixture is separated into isocyanate, solvent and gas phase (comprising phosgene and hydrogen chloride), preferably by means of simple phase separation, if appropriate with addition of a further solvent. Small amounts of isocyanate remaining in the ionic liquid can, if necessary, be separated from the ionic liquid by means of additional extraction or else crystallization. The isocyanate can be freed of by-products by customary purification methods. Phosgene and hydrogen chloride can, for example, be separated from one another by distillation.

The ionic liquid which has been separated off can subsequently be recirculated as solvent.

The use of ionic liquids allows the formation of solids to be prevented and the costly apparatus for handling solids thus to be dispensed with. In addition, the amine hydrochlorides formed react with the phosgene more quickly. Furthermore, the reaction can be carried out at low pressures and/or temperatures. This results in a lower phosgene holdup, a higher STY and better selectivities.

The invention is illustrated by the following examples.

EXAMPLE 1

Preparation of MDI in Monochlorobenzene (MOB)

75 g of MOB were placed in a 500 ml four-neck flask provided with stirrer, internal thermometer, immersed inlet tube for phosgene and heated feed line. This was saturated with phosgene at 120° C. A solution of MDA in MOB (50 g of MDA in 90 g of MOB) was metered in over a period of 1 hour while continuing to introduce phosgene. After the reaction was complete, the mixture was stripped free of phosgene by means of nitrogen.

A conversion of 44% was found in the solids containing crude product mixture (about 60% by weight of amine hydrochloride, according to elemental analysis).

EXAMPLE 2

Preparation of MDI in Methylimidazolium Chloride 75 g of methylimidazolium chloride (MIA-HCl) were placed in a 500 ml four-neck flask provided with stirrer, internal thermometer, immersed inlet tube for phosgene and heated feed line. This was saturated with phosgene at 130CC. A solution of MDA in MIA-HCl (50 g of MDA in 88 g of MIA-HCl) was metered in over a period of 1 hour while continuing to introduce phosgene. After the reaction was complete, the mixture was stripped free of phosgene by means of nitrogen.

The gas chromatogram of the homogeneous crude product mixture indicated complete conversion.

EXAMPLE 3

Preparation of MDI in 1-butyl-3-methylimidazolium chloride 200 g of 1-butyl-3-methylimidazolium chloride (BMIM-Cl) were placed in a 500 ml four-neck flask provided with stirrer, internal thermometer, immersed inlet tube for phosgene and heated feed line. This was saturated with phosgene at 120° C. A solution of MDA in BMIM-Cl (50 g of MDA in 100 g of BMIM-Cl) was metered in over a period of 4 hours while continuing to introduce phosgene. After the reaction was complete, the mixture was stripped free of phosgene by means of nitrogen.

The gas chromatogram of the homogeneous crude product mixture indicated complete conversion.

EXAMPLE 4

Preparation of HDI in 1-butyl-3-methylimidazolium chloride 200 g of 1-butyl-3-methylimidazolium chloride (BMIM-Cl) were placed in a 500 ml four-neck flask provided with stirrer, internal thermometer, immersed inlet tube for phosgene and heated feed line. This was saturated with phosgene at 120° C. A solution of HDA in BMIM-Cl (65 g of HDA in 100 g of BMIM-Cl) was metered in over a period of 3 hours while continuing to introduce phosgene. After the reaction was complete, the mixture was stripped free of phosgene by means of nitrogen.

The gas chromatogram of the homogeneous crude product mixture indicated complete conversion.

EXAMPLE 5

Preparation of MDI in Methylimidazolium ChloridexHCl 75 g of methylimidazolium chloride (MIA-HCl) were placed in a 500 ml four-neck flask provided with stirrer, internal thermometer, immersed inlet tube for phosgene and heated feed line. This was saturated with hydrogen chloride gas at 120° C. It was subsequently saturated with phosgene at 120° C. A solution of MDA in MIA-HCl which had been saturated at with HCl gas at room temperature (50 g of MDA in 88 g of MIA×1.8 HCl) was metered in over a period of 1 hour while continuing to introduce phosgene. After the reaction was complete, the mixture was stripped free of phosgene by means of nitrogen.

The gas chromatogram of the homogeneous crude product mixture indicated complete conversion.

EXAMPLE 6

Preparation of MDI in 1-ethyl-3-methylimidazolium chloridexHCl 75 g of 1-ethyl-3-methylimidazolium (EMIM-Cl) were placed in a 500 ml four-neck flask provided with stirrer, internal thermometer, immersed inlet tube for phosgene and heated feed line. This was saturated with hydrogen chloride gas at 120° C. It was subsequently saturated with phosgene at 120° C. A solution of MDA in EMIM-Cl which had been saturated at with HCl gas at room temperature (50 g of MDA in 93 g of EMIM-Cl×1.3 HCl) was metered in over a period of 1 hour while continuing to introduce phosgene. After the reaction was complete, the mixture was stripped free of phosgene by means of nitrogen. The gas chromatogram of the homogeneous crude product mixture indicated complete conversion.

EXAMPLE 7

Preparation of MDI in Ethylmethylimidazolium Chloride 2.0 g of MDA×HCl together with 100.5 g of EMIM Cl (ethylmethylimidazolium chloride) were placed in a 400 ml pressure autoclave. 7.2 g of phosgene are introduced into this solution at 120° C. The phosgenation takes place under the autogenous pressure of the reaction system at the reaction temperature.

| Times | Example 7 Yield % | Example 8 Yield % |
|---|---|---|
| 39 | 34 | 28 |
| 58 | 57 | 34 |
| 86 | 84 | 38 |

EXAMPLE 8

Preparation of MDI in Monochlorobenzene 352.0 g of MDA×HCl together with 100 g of monochlorobenzene were placed in a 400 ml pressure autoclave. 7.5 g of phosgene are introduced into this solution at 120° C. The phosgenation takes place under the autogenous pressure of the reaction system at the reaction temperature.

The invention claimed is:

1. A process for preparing polyisocyanates, comprising:
reacting primary amines with phosgene in the presence of an ionic liquid as a solvent, wherein the ionic liquid is at least one selected from the group consisting of 1-butyl-3-methylimidazolium chloride, 1-ethyl-3-methylimidazolium chloride, 1-butyl-4-methylpyridinium chloride, 1-butylimidazolium chloride, and 1-methylimidazolium chloride.

2. The process according to claim 1, wherein the primary amine is present as a solution of amine hydrochloride in the ionic liquid.

3. The process according to claim 1, wherein the ionic liquid comprises hydrogen chloride.

4. The process according to claim 3, wherein a mol % ratio of hydrogen chloride to ionic liquid is from >0 to 400 mol %.

5. The process according to claim 4, wherein the mol % ratio of hydrogen chloride to ionic liquid is from 5 to 300 mol %.

6. The process according to claim 4, wherein the mol % ratio of hydrogen chloride to ionic liquid is from 10 to 150 mol %.

* * * * *